(12) United States Patent (10) Patent No.: US 8,509,874 B2
Hu et al. (45) Date of Patent: Aug. 13, 2013

(54) METHOD FOR NON-CONTRAST ENHANCED PULMONARY VEIN MAGNETIC RESONANCE IMAGING

(75) Inventors: Peng Hu, Brookline, MA (US); Reza Nezafat, Newton, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 383 days.

(21) Appl. No.: 12/846,182

(22) Filed: Jul. 29, 2010

(65) Prior Publication Data

US 2011/0028829 A1 Feb. 3, 2011

Related U.S. Application Data

(60) Provisional application No. 61/229,881, filed on Jul. 30, 2009.

(51) Int. Cl.
*A61B 5/055* (2006.01)

(52) U.S. Cl.
USPC .............................. 600/410; 600/411; 600/413

(58) Field of Classification Search
USPC ................. 600/410–411, 413, 419; 324/306, 324/307, 309
See application file for complete search history.

(56) References Cited

U.S. PATENT DOCUMENTS

| 5,528,144 | A | 6/1996 | Gullapalli et al. |
| 6,498,946 | B1 | 12/2002 | Foo et al. |
| 6,564,080 | B1 | 5/2003 | Kimura |
| 7,315,756 | B2 | 1/2008 | Yarnykh et al. |
| 8,010,181 | B2 * | 8/2011 | Smith et al. .................... 600/424 |
| 2010/0160765 | A1 * | 6/2010 | Marrouche et al. ........... 600/410 |

* cited by examiner

*Primary Examiner* — Ruth S Smith

(74) *Attorney, Agent, or Firm* — Quarles & Brady, LLP

(57) ABSTRACT

A system and method for non-contrast enhanced pulmonary vein magnetic resonance imaging substantially suppresses the signal from cardiac tissue adjacent to the left atrium and pulmonary vein is provided. Significant conspicuity of the left atrium and pulmonary vein versus adjacent anatomical structures is produced. In this manner, more accurate measurements of pulmonary vein ostia size are facilitated, as well as more accurate registration of imaging volumes with a radiofrequency ablation catheter during pulmonary vein isolation procedures. In addition, more robust three-dimensional volume views of the left atrium and pulmonary vein are produced without the administration of contrast agents.

18 Claims, 3 Drawing Sheets

METHOD FOR NON-CONTRAST ENHANCED PULMONARY VEIN MAGNETIC RESONANCE IMAGING

CROSS-REFERENCE TO RELATED APPLICATIONS

This application claims the benefit of U.S. Provisional patent application Ser. No. 61/229,881 filed on Jul. 30, 2009, and entitled "METHOD FOR NON-CONTRAST ENHANCED PULMONARY VEIN MAGNETIC RESONANCE IMAGING".

BACKGROUND OF THE INVENTION

The present invention related to medical imaging and, more particularly, to systems and methods for non-contrast enhanced pulmonary vein MR imaging, for example, using magnetic resonance imaging (MRI).

In MRI, when a substance such as human tissue is subjected to a uniform magnetic field (polarizing field $B_0$), the individual magnetic moments of the nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped", into the x-y plane to produce a net transverse magnetic moment $M_{xy}$. A signal is emitted by the excited nuclei or "spins", after the excitation signal $B_1$ is terminated, and this signal may be received and processed to form an image.

When utilizing these "MR" signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

The measurement cycle used to acquire each MR signal is performed under the direction of a pulse sequence produced by a pulse sequencer. Clinically available MRI systems store a library of such pulse sequences that can be prescribed to meet the needs of many different clinical applications. Research MRI systems include a library of clinically proven pulse sequences and they also enable the development of new pulse sequences.

The MR signals acquired with an MRI system are signal samples of the subject of the examination in Fourier space, or what is often referred to in the art as "k-space." Each MR measurement cycle, or pulse sequence, typically samples a portion of k-space along a sampling trajectory characteristic of that pulse sequence. Most pulse sequences sample k-space in a raster scan-like pattern sometimes referred to as a "spin-warp", a "Fourier", a "rectilinear", or a "Cartesian" scan. The spin-warp scan technique employs a variable amplitude phase encoding magnetic field gradient pulse prior to the acquisition of MR spin-echo signals to phase encode spatial information in the direction of this gradient. In a two-dimensional implementation ("2DFT"), for example, spatial information is encoded in one direction by applying a phase encoding gradient, $G_y$, along that direction, and then a spin-echo signal is acquired in the presence of a readout magnetic field gradient, $G_x$, in a direction orthogonal to the phase encoding direction. The readout gradient present during the spin-echo acquisition encodes spatial information in the orthogonal direction. In a typical 2DFT pulse sequence, the magnitude of the phase encoding gradient pulse, $G_y$, is incremented, $\Delta G_y$, in the sequence of measurement cycles, or "views" that are acquired during the scan to produce a set of k-space MR data from which an entire image can be reconstructed.

Atrial fibrillation is one of the most common sustained cardiac arrhythmias, afflicting over 2.2 million Americans and responsible for approximately one-third of arrhythmic hospitalizations. Following the recognition that ectopic beats in the pulmonary veins are a source of atrial fibrillation, pulmonary vein isolation (PVI) using radiofrequency (RF) ablation has become an accepted treatment. Imaging, such as using MRI, is commonly performed prior to the RF ablation treatment in order to identify the anatomic features of the pulmonary vein and left atrium and to assist procedural planning. Exemplary anatomic features include the number of pulmonary veins, pulmonary vein ostia size and orientation. Post-ablation pulmonary vein imaging is also conventionally performed in order to detect post-procedural complications, such as pulmonary vein stenosis.

Both multi-detector computed tomography (CT) and MRI are commonly used to image the pulmonary vein and left atrium; however, MRI offers the advantage of not exposing the patient to ionizing radiation or iodinated contrast. In current clinical practice, contrast enhanced MR angiography is conventionally used to perform imaging of the left atrium and pulmonary veins with a non-ECG gated spoiled gradient echo (GRE) imaging sequence.

Magnetic resonance angiography (MRA) uses the magnetic resonance phenomenon to produce images of the human vasculature. To enhance the diagnostic capability of MRA a contrast agent, such as gadolinium, is often injected into the patient prior to the MRA scan. Sampling of the central lines of k-space during peak arterial enhancement is key to the success of a CE MRA exam. If the central lines of k-space are acquired prior to the arrival of contrast, severe image artifacts can limit the diagnostic information in the image. Moreover, this data acquisition typically occurs during a prolonged breath-hold by the patient, which poses difficulties for those patients with atrial fibrillation. Since the pulmonary veins and left atrium are in close proximity to the right atrium, and great vessels such as the aorta, pulmonary artery, and superior and inferior vena cava, in the absence of contrast media, lack of contrast between the pulmonary vein and these adjacent structures is commonly observed. This lack of image contrast compromises pulmonary vein conspicuity. Data acquisition without ECG gating also poses difficulties for imaging the pulmonary veins, since doing so results in image blurring and over-estimation of pulmonary vein size. With the recent recognition of the association of nephrogenic systemic fibrosis (NSF) and gadolinium-based contrast media in patients with renal impairment, there has been increased interest in non-contrast enhanced MRA techniques.

One such non-contrast enhanced MRA technique is pulsed arterial spin labeling (ASL), which has been used in coronary, renal, and carotid artery MRA. In these methods, a slice selective inversion pulse is commonly applied proximal to the vessel of interest to label the in-flowing spins. After an inversion time (TI), during which the labeled spins flow into imaging slab, imaging is performed. To enhance the contrast, imaging is typically performed twice; once with and once without the labeling inversion pulse. A subtraction of the two data sets provides an angiogram with greatly suppressed stationary background tissue. In subtracting these data sets, however, pulsed ASL methods can introduce phase cancellations and produce signal-to-noise ratio (SNR) loss. To eliminate the need for subtraction, which also doubles imaging time, a modified double-inversion sequence has been proposed for coronary artery MRI, in which a non-selective inversion pulse is immediately followed by a two-dimensional selective pulse that locally re-inverts the ascending aorta. Aside from the undesirable increase in imaging time required for such double-inversion methods, lack of conspicuity between pulmonary veins and the left atrium and their adjacent structures is still prevalent in pulsed ASL methods, which prevents these methods from widespread clinical use.

It would therefore be desirable to provide a system and method for imaging of the pulmonary vein that does not rely on the use of an exogenous contrast agent or undesired ionizing radiation and that can produce images marked by significant contrast-to-noise ratio (CNR) between the pulmonary veins and adjacent anatomical structures. Moreover, it would be desirable to provide such a method in which breath-holding is not required by the subject under examination.

SUMMARY OF THE INVENTION

The present invention overcomes the aforementioned drawbacks by providing a non-contrast enhanced MR imaging method that produces images of a subject's pulmonary veins, in which there is significant conspicuity between both the pulmonary veins and left atrium and the adjacent anatomic structures. In particular, a method that substantially suppresses the signal from cardiac tissue adjacent to the left atrium and pulmonary vein, resulting in significant enhancement in the conspicuity of the left atrium and pulmonary vein, is provided. The method facilitates more accurate measurements of pulmonary vein ostia size. In addition, accurate registration of MR imaging volumes with an ablation catheter in a pulmonary vein isolation (PVI) procedure can be performed. Moreover, robust three-dimensional volume views of the left atrium and pulmonary vein, which are used for the PVI procedure, are produced without the need to administer contrast agents.

In accordance with one aspect of the invention, a method is provided for producing an image of a subject with a magnetic resonance imaging (MRI) system. The method includes identifying a desired imaging slab extending parallel to an imaging plane and performing a pulse sequence with the MRI system. The pulse sequence includes applying an inversion recovery radiofrequency (RF) pulse in an inversion slab oriented in an inversion plane that extends not parallel to the imaging plane and substantially not including a pulmonary vein and allowing a selected inversion time (TI) to pass following the application of the inversion recovery RF pulse. Following the TI, the pulse sequence includes acquiring image data from the desired imaging slab to then reconstruct an image of the subject from the acquired image data.

In accordance with another aspect of the invention, a method is provided for producing an image of a subject's pulmonary vein with a magnetic resonance imaging (MRI) system. The method includes acquiring an electrocardiogram (ECG) signal from the subject to at least identify an R-wave in the acquired ECG signal and performing a pulse sequence with the MRI system. During the pulse sequence and after identifying an occurrence of an R-wave in the acquired ECG signal, the MRI system is caused to apply an inversion recovery radiofrequency (RF) pulse in an inversion slab that is oriented in a plane not parallel to an imaging plane and that does not substantially include the pulmonary vein. The MRI system is also caused to acquire image data in an imaging slab parallel to the imaging plane beginning at a selected inversion time (TI) following the application of the inversion recovery RF pulse and acquire navigator echo data. The method includes reconstructing an image including the subject's pulmonary vein from the acquired image data and using the navigator echo data.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
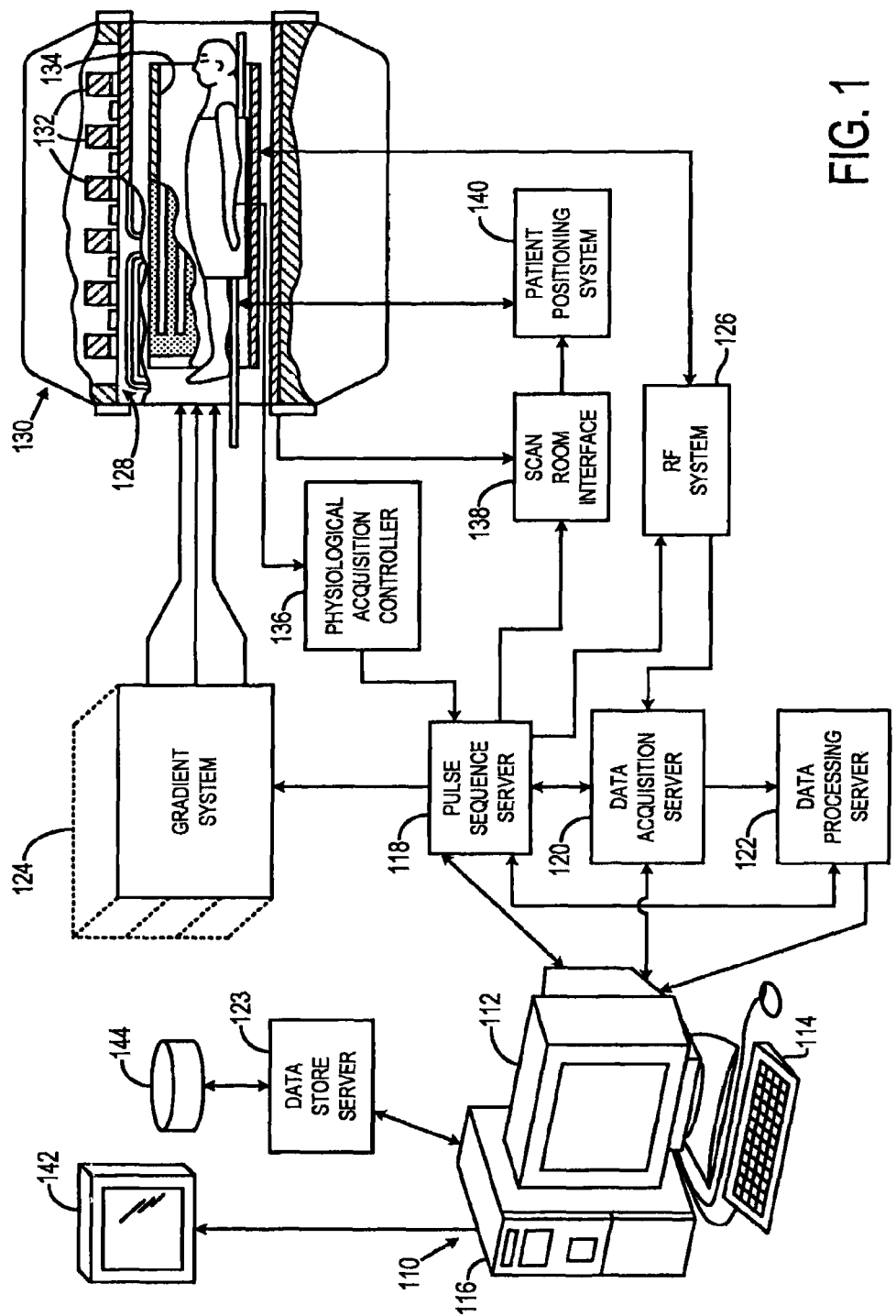
FIG. 1 is a block diagram of an MRI system that employs the present invention.

Referring particularly to FIG. 1, the present invention is employed in an MRI system. The MRI system includes a workstation 110 having a display 112 and a keyboard 114. The workstation 110 includes a processor 116 that is a commercially available programmable machine running a commercially available operating system. The workstation 110 provides the operator interface that enables scan prescriptions to be entered into the MRI system. The workstation 110 is coupled to four servers: a pulse sequence server 118; a data acquisition server 120; a data processing server 122, and a data store server 123. The workstation 110 and each server 118, 120, 122 and 123 are connected to communicate with each other.

The pulse sequence server 118 functions in response to instructions downloaded from the workstation 110 to operate a gradient system 124 and an RF system 126. Gradient waveforms necessary to perform the prescribed scan are produced and applied to the gradient system 124 that excites gradient coils in an assembly 128 to produce the magnetic field gradients $G_x$, $G_y$, and $G_z$ used for position encoding MR signals. The gradient coil assembly 128 forms part of a magnet assembly 130 that includes a polarizing magnet 132 and a whole-body RF coil 134.

RF excitation waveforms are applied to the RF coil 134 by the RF system 126 to perform the prescribed magnetic resonance pulse sequence. Responsive MR signals detected by the RF coil 134 or a separate local coil (not shown in FIG. 1) are received by the RF system 126, amplified, demodulated, filtered and digitized under direction of commands produced by the pulse sequence server 118. The RF system 126 includes an RF transmitter for producing a wide variety of RF pulses used in MR pulse sequences. The RF transmitter is responsive to the scan prescription and direction from the pulse sequence server 118 to produce RF pulses of the desired frequency, phase and pulse amplitude waveform. The generated RF pulses may be applied to the whole body RF coil 134 or to one or more local coils or coil arrays (not shown in FIG. 1).

The RF system 126 also includes one or more RF receiver channels. Each RF receiver channel includes an RF amplifier that amplifies the MR signal received by the coil to which it is connected and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2},$$

and the phase of the received MR signal may also be determined:

$$\varphi = \tan^{-1}\left(\frac{Q}{I}\right).$$

The pulse sequence server 118 also optionally receives patient data from a physiological acquisition controller 136. The controller 136 receives signals from a number of different sensors connected to the patient, such as ECG signals from electrodes or respiratory signals from a bellows. Such signals are typically used by the pulse sequence server 118 to synchronize, or "gate", the performance of the scan with the subject's respiration or heart beat.

The pulse sequence server 118 also connects to a scan room interface circuit 138 that receives signals from various sensors associated with the condition of the patient and the magnet system. It is also through the scan room interface circuit 138 that a patient positioning system 140 receives commands to move the patient to desired positions during the scan.

The digitized MR signal samples produced by the RF system 126 are received by the data acquisition server 120. The data acquisition server 120 operates in response to instructions downloaded from the workstation 110 to receive the real-time MR data and provide buffer storage such that no data is lost by data overrun. In some scans the data acquisition server 120 does little more than pass the acquired MR data to the data processor server 122. However, in scans that require information derived from acquired MR data to control the further performance of the scan, the data acquisition server 120 is programmed to produce such information and convey it to the pulse sequence server 118. For example, during prescans MR data is acquired and used to calibrate the pulse sequence performed by the pulse sequence server 118. Also, navigator signals may be acquired during a scan and used to adjust RF or gradient system operating parameters or to control the view order in which k-space is sampled. And, the data acquisition server 120 may be employed to process MR signals used to detect the arrival of contrast agent in a magnetic resonance angiography (MRA) scan. In all these examples the data acquisition server 120 acquires MR data and processes it in real-time to produce information that is used to control the scan.

The data processing server 122 receives MR data from the data acquisition server 120 and processes it in accordance with instructions downloaded from the workstation 110. Such processing may include, for example: Fourier transformation of raw k-space MR data to produce two or three-dimensional images; the application of filters to a reconstructed image; the performance of a backprojection image reconstruction of acquired MR data; the calculation of functional MR images; the calculation of motion or flow images, etc.

Images reconstructed by the data processing server 122 are conveyed back to the workstation 110 where they are stored. Real-time images are stored in a data base memory cache (not shown) from which they may be output to operator display 112 or a display 142 that is located near the magnet assembly 130 for use by attending physicians. Batch mode images or selected real time images are stored in a host database on disc storage 144. When such images have been reconstructed and transferred to storage, the data processing server 122 notifies the data store server 123 on the workstation 110. The workstation 110 may be used by an operator to archive the images, produce films, or send the images via a network to other facilities.

Figure 2:
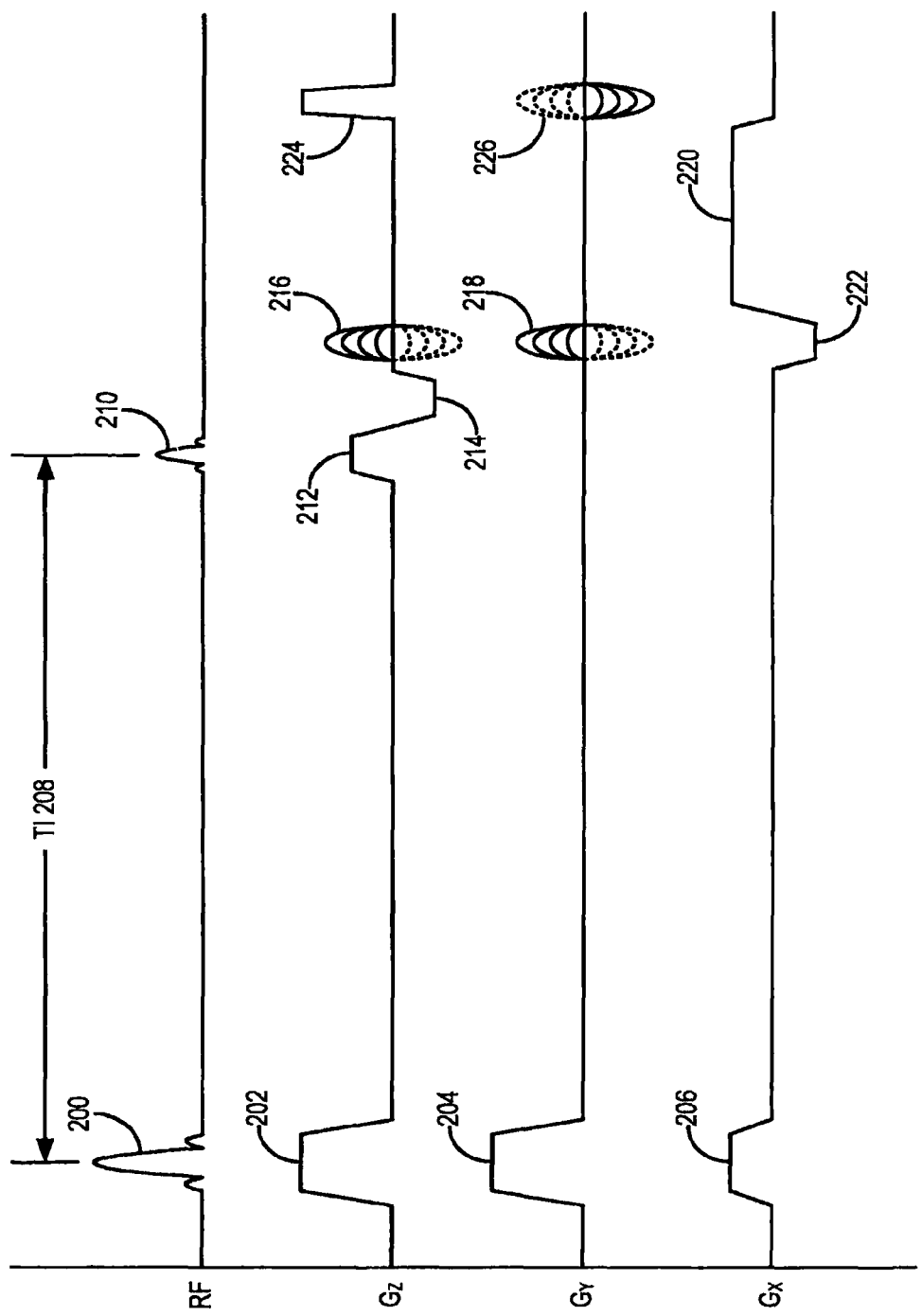
FIG. 2 is a pictorial representation of an exemplary pulse sequence employed by the MRI system of FIG. 1 when practicing the present invention.

An exemplary pulse sequence employed when practicing the present invention is illustrated in FIG. 2. In general, the pulse sequence utilizes an inversion recovery (IR) radiofrequency (RF) pulse that is applied to a slab that covers the left atrium, and which is followed by an inversion time (TI) period before gradient echo imaging is performed to acquire image data. An exemplary slab selection for the IR pulse is on the order of 60 millimeters (mm) thick and oriented in the sagittal plane; however, as will be described below in detail, other slab thicknesses and orientations can also be employed. The location of the slab is generally selected such that the inversion pulse inverts the spins in the left atrium, right atrium, aorta, and superior and inferior vena cava. During the TI period, the inverted spins relax back towards thermal equilibrium, while pulmonary venous blood flows into the left atrium from the pulmonary vein, and blood from the superior and inferior vena cava flows into the right atrium. Because the inversion slab does not substantially contain the pulmonary vein, the pulmonary venous blood remains un-inverted, resulting in higher left atrium and pulmonary vein signal when imaging at TI. It should be appreciated by those skilled in the art, however, that the inversion slab need not be oriented in the sagittal plane. In the alternative, the inversion slab can be oriented in the coronal plane or in any such oblique plane not parallel with the axial plane.

The choice of the TI period is a balance between two considerations. First, it is desired that signals from myocardial tissue and in-flowing blood from the vena cava be substantially suppressed. The TI needed to null blood and myocardial tissue is different due to their different $T_1$ values. To this end, the TI period is set with more concern for the suppression of vena cava blood since undesired signal from myocardial tissue can be adequately suppressed using $T_2$ preparation if desired.

The second consideration for setting the TI period is that it is desired to allow adequate time for pulmonary venous blood to flow into the left atrium. Thus, if the TI period is too long, the contrast enhancement due to the inversion pulse will diminish as the inverted blood flows out of the heart and the un-inverted blood replaces it. On the other hand, if the TI is too short, the fresh, un-inverted pulmonary venous blood is less likely to replace the inverted blood in the left atrium, causing signal loss. Therefore, the TI period should be selected such that the amount of pulmonary venous flow during the TI period is substantial, in order to achieve significant left atrium signal enhancement from in-flowing fresh pulmonary venous blood. In a typical cardiac cycle, there is high pulmonary venous blood flow during early ventricular systole and mid-diastole; therefore, it is advantageous to time the inversion pulse to be applied substantially immediately after an R-wave trigger. That is, it is desirable to apply the inversion pulse at the start of ventricular systole, using a contemporaneously recorded electrocardiogram (ECG) signal.

In general, signal in the right atrium and descending aorta is suppressed well with a TI between 350-500 ms and moderately as the TI increases to around 550-600 ms. In addition, there is typically significant signal void in the left atrium when TI is set around 350-400 ms, due to an insufficient period of time for non-inverted pulmonary venous blood to flow into the left atrial cavity. Following the foregoing considerations, a TI of around approximately 400-600 ms, for example, 500 ms, may be utilized to achieve acceptable trade-off between adjacent structure suppression and signal uniformity in the left atrium.

The general considerations for selecting the location and thickness of the inversion slab is that the left-right dimension of the left atrium be substantially covered by the inversion volume and that the proximal pulmonary vein not be substantially covered. When the proximal pulmonary vein is contained in the inversion volume, pulmonary venous blood that later flows into the left atrium is inverted, potentially resulting in undesirable signal voids. The choice of inversion slab thickness is also selected such that it results in suppression of signals arising from tissues between the left atrium and proximal pulmonary vein. This facilitates more accurate measurement of pulmonary vein ostia size. An inversion slab thickness around, for example, approximately 50-80 mm provides suitable pulmonary vein and left atrium visualization. As noted above, the inversion slab is oriented in the sagittal plane; however, it should be appreciated by those skilled in the art that the inversion slab can also be oriented in the coronal plane, or in any such oblique plane not parallel with the axial plane.

Referring now to the exemplary pulse sequence illustrated in FIG. 2, the pulse sequence begins with the application of an inversion recovery RF pulse 200 in the presence of three slab-selective gradients: one along the $G_z$-axis 202, one along the $G_y$-axis 204, and one along the $G_z$-axis 206. The result of playing out the inversion recovery pulse 200 in the presence of these gradients is the inversion of magnetization in the slab volume defined in the z-direction by the $G_z$ slab-selective gradient 202, in the y-direction by the $G_y$ slab-selective gradient 204, and in the x-direction by the $G_z$ slab-selective gradient 206. The application of the inversion recovery pulse 200 is followed by a TI period 208. After the TI period 208 passes, an imaging sequence is initiated. An exemplary imaging sequence is a so-called turbo field echo (TFE) sequence, which is, in general, a gradient echo sequence that is run with a very short repetition time (TR) period and echo time (TE). For example, a TR on the order of 5 ms is employed. Such TFE pulse sequences are also referred to as magnetization prepared gradient echo and "Turbo FLASH" pulse sequences.

An exemplary TFE imaging sequence is shown in FIG. 2, and commences by the selective excitation of the entire region-of-interest with the application of an RF excitation pulse 210 in the presence of a slab-selective gradient pulse 212. The frequency content of the excitation pulse 210 and the amplitude of the slab-selective gradient 212 are selected to produce transverse magnetization in the region that is the subject of the 3D scan. The slab-selective gradient 212 includes a negative gradient lobe 214 that acts to rephase the spins in preparation for phase encoding and readout.

Phase encoding is performed along two axes, such as, for example, the $G_z$-axis and the $G_y$-axis. The $G_z$-axis encoding is accomplished by applying a $G_z$ phase encoding pulse 216 and the y-axis encoding is accomplished by applying a $G_y$ phase encoding pulse 218. The magnitude of the phase encoding pulses 216 and 218 are stepped through a series of positive and negative values during the scan, but each is set to one value during each repetition of the pulse sequence. As will be described below, the order in which these phase encoding pulses 216 and 218 are stepped through a set of values determines the k-space sampling order. The magnitude of a phase encoding gradient pulse is determined by the integral of its amplitude over its duration, that is, its area. In most pulse sequences, the duration is kept constant and the phase encoding pulse magnitude is stepped through its value by changing its amplitude.

After phase encoding the transverse magnetization, an MR signal is read-out in the presence of a $G_x$ read-out gradient 220. This read-out gradient 220 is preceded by a negative $G_x$ gradient lobe 222 that acts to produce a gradient refocused echo signal in the usual fashion. Each repetition of the imaging sequence is concluded by the application of a spoiler gradient pulse 224 along the $G_z$-axis and a rewinder gradient pulse 226 along the $G_y$-axis in order to prepare the magnetization for the next repetition of the imaging sequence, which follows thereafter. The spoiler pulse 224 dephases transverse magnetization and the rewinder pulse 226 refocuses transverse magnetization along the y-axis in preparation for the next repetition of the imaging sequence. The rewinder pulse 226 is equal in magnitude, but opposite in polarity with the $G_y$ phase encoding pulse 218.

The acquisition of data in the foregoing manner is considered as sampling a three-dimensional k-space. Two of the dimensions, $k_y$ and $k_z$, are sampled by applying different phase encoding gradients 218 and 216 during each repetition of the imaging sequence, and each acquired line of k-space data includes, for example, 256 samples of the echo signal along a line in the $k_x$-direction. The imaging sequence is repeated for as many repetitions as are necessary to sample all of the desired $k_y$ and $k_z$ values.

By way of example, $k_y$ may assume 128 different values and $k_z$ may have 64 values. In such an example, the number of repetitions of the TFE imaging sequence in FIG. 2 would be 128×64, or 8192 repetitions. Typically, the desired values of $k_y$ and $k_z$ are sampled with two nested loops. For example, an inner loop increments $k_y$ through its 128 values and after all such samples have been acquired for a given value of $k_z$, the outer loop increments $k_z$. This process continues until all 128 values of $k_y$ have been sampled at each of the 64 values of $k_z$.

The aforementioned pulse sequence can be supplemented to further improve the images reconstructed from the acquired image data. For example, during the TI period, spectrally selective fat saturation can be employed to substantially suppress signals arising from adipose tissue surrounding the heart. Furthermore, navigator echo data can be acquired through the inclusion of an navigator echo sequence prior or subsequent to data acquisition. This navigator echo data is then utilized to compensate for respiratory motion of the subject that occurred during the acquisition of the image data. In this manner, data can be acquired without the need for lengthy breath-holding by the subject undergoing examination. Exemplary navigator echo sequences include one-dimensional, orbital, spherical, and cloverleaf type navigator echo sequences.

Figure 3:
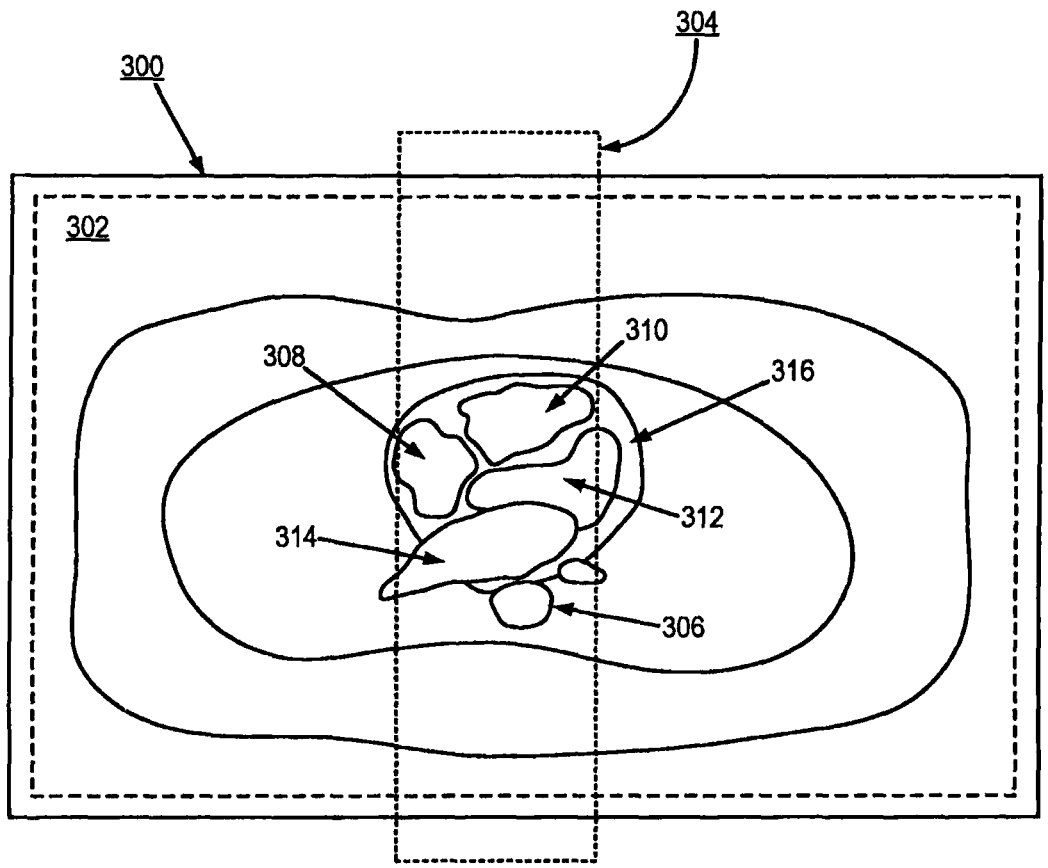
FIG. 3 is a pictorial representation of an exemplary inversion slab and imaging volume orientation with respect to a subject undergoing examination.

By way of example, and referring now particularly to FIG. 3, an axial slice of subject positioned in the field-of-view (FOV) 300 of an MRI system is illustrated. An imaging volume 302 includes the axial slice shown and similar parallel slices extending along a shared longitudinal axis. From this imaging volume, images of the subject are acquired using the aforementioned pulse sequence. In accordance with the aforementioned pulse sequence, an inversion slab 304 is selected and an inversion recovery RF pulse applied thereto. In this example, the inversion slab 304 is located such that the spins in the aorta 306, right atrium 308, right ventricle 310, the left atrium (not shown), and most of the left ventricle 312 and a portion of the pulmonary vein 314 are inverted. However, the inversion slab 304 is located such that the blood flowing into the left atrium from the pulmonary vein 314 around the preselected, inversion time period is substantially un-inverted. The stationary spins in the myocardium 316 are also inverted; however, as discussed above, the signal arising from these spins is not necessarily substantially suppressed when data acquisition occurs.

Therefore, a non-contrast enhanced MR imaging method is provided that produces images of a subject's pulmonary veins, in which there is significant conspicuity between both the pulmonary veins and left atrium and the adjacent anatomic structures. The method substantially suppresses the signal from cardiac tissue adjacent to the left atrium and pulmonary vein, resulting in significant enhancement in the conspicuity of the left atrium and pulmonary vein. The method facilitates more accurate measurements of pulmonary vein ostia size. In addition, accurate registration of MR imaging volumes with an ablation catheter in a pulmonary vein isolation (PVI) procedure can be performed. Moreover, robust three-dimensional volume views of the left atrium and pulmonary vein, which are used for the PVI procedure, are produced without the need to administer contrast agents.

The present invention has been described in terms of one or more preferred embodiments, and it should be appreciated that many equivalents, alternatives, variations, and modifications, aside from those expressly stated, are possible and within the scope of the invention.

We claim:

1. A method for producing a non-contrast enhanced image of a subject with a magnetic resonance imaging (MRI) system, the steps comprising:
   a) identifying a desired imaging slab extending parallel to an imaging plane including at least a portion of the pulmonary vein;
   b) performing a pulse sequence with the MRI system that includes:
      i) applying an inversion recovery radiofrequency (RF) pulse in an inversion slab oriented in an inversion plane that extends not parallel to the imaging plane and not including the pulmonary vein of the subject;
      ii) allowing a selected inversion time (TI) to pass following the application of the inversion recovery RF pulse;
      iii) following the TI, acquiring image data from the desired imaging slab; and
   c) reconstructing an image of the subject including at least the portion of the pulmonary vein from the acquired image data.

2. The method of claim 1 wherein the desired inversion slab extends in a substantially sagittal orientation through the subject.

3. The method of claim 1 wherein the desired inversion slab extends in a substantially coronal orientation through the subject.

4. The method as recited in claim 1 wherein the image slab also extends through at least a portion of the left atrium.

5. The method of claim 1 wherein the TI is selected to be approximately 350 to 500 ms in duration.

6. The method of claim 1 wherein the desired inversion slab has a thickness of approximately 60 mm.

7. The method of claim 1 wherein step b) further includes acquiring an electrocardiogram (ECG) signal from the subject and identifying an R-wave in the acquired ECG signal and step b)i) includes applying the desired inversion RF pulse after the occurrence of an R-wave in the acquired ECG signal.

8. The method of claim 1 wherein step b)iii) includes acquiring navigator image data in addition to the image data and step c) includes reconstructing a navigator image from the navigator image data.

9. The method of claim 8 wherein step c) includes using the navigator image to compensate for respiratory motion when reconstructing the image of the subject from the acquired image data.

10. The method of claim 1 wherein the inversion slab extends through at least a portion of an aorta, right atrium, right ventricle, left ventricle, and left atrium of the subject.

11. A method for producing an non-contrast enhanced image of a subject's pulmonary vein with a magnetic resonance imaging (MRI) system, the steps comprising:
    a) acquiring an electrocardiogram (ECG) signal from the subject to at least identify an R-wave in the acquired ECG signal;
    b) performing a pulse sequence with the MRI system that causes the MRI system to:
       i) after identifying an occurrence of an R-wave in the acquired ECG signal, apply an inversion recovery radiofrequency (RF) pulse in an inversion slab that is oriented in a plane not parallel to an imaging plane and that does not include the pulmonary vein;
       ii) acquire image data in an imaging slab parallel to the imaging plane beginning at a selected inversion time (TI) following the application of the inversion recovery RF pulse;
       iii) acquire navigator echo data;
    c) reconstructing an image including the subject's pulmonary vein from the acquired image data and using the navigator echo data; and
    wherein the imaging slab extends through at least a portion of the pulmonary vein.

12. The method of claim 11 wherein the inversion slab extends in one of a substantially sagittal orientation through the subject and a substantially coronal orientation through the subject.

13. The method of claim 11 wherein the TI is selected to be approximately 350 to 500 ms in duration.

14. The method of claim 11 wherein the desired inversion slab has a thickness of approximately 60 mm.

15. The method of claim 11 wherein step c) includes reconstructing a navigator image from the navigator echo data and using the navigator image to compensate for respiratory motion when reconstructing the image of the subject from the acquired image data.

16. The method of claim 11 wherein the inversion slab extends through at least a portion of an aorta, right atrium, right ventricle, left ventricle, and left atrium of the subject.

17. The method of claim 11 further comprising d) determining, using the reconstructed image of the subject, a pulmonary vein ostia size.

18. The method of claim 11 further comprising d) registering the reconstructed image of the subject with a radiofrequency ablation catheter during pulmonary vein isolation procedure.

* * * * *

UNITED STATES PATENT AND TRADEMARK OFFICE
CERTIFICATE OF CORRECTION

PATENT NO. : 8,509,874 B2  
APPLICATION NO. : 12/846182  
DATED : August 13, 2013  
INVENTOR(S) : Peng Hu et al.

Page 1 of 1

It is certified that error appears in the above-identified patent and that said Letters Patent is hereby corrected as shown below:

On the Title Page, Item (54) and in the specification, Column 1, line 1, Title, "METHOD FOR" should read --SYSTEM AND METHOD FOR--.

In the Claims:

Column 10, Claim 11, line 14, "an" should be --a--.

Signed and Sealed this  
Fifteenth Day of October, 2013

Teresa Stanek Rea  
*Deputy Director of the United States Patent and Trademark Office*